United States Patent
Lucas et al.

(10) Patent No.: US 11,673,913 B2
(45) Date of Patent: Jun. 13, 2023

(54) PREPARATION OF RECOMBINANT TETRAMERIC N-ACETYLATED ALPHA-SYNUCLEIN

(71) Applicant: Virginia Commonwealth University, Richmond, VA (US)

(72) Inventors: Heather R. Lucas, Richmond, VA (US); Ricardo D. Fernandez, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 914 days.

(21) Appl. No.: 16/408,711

(22) Filed: May 10, 2019

(65) Prior Publication Data
US 2019/0345195 A1    Nov. 14, 2019

Related U.S. Application Data

(60) Provisional application No. 62/669,479, filed on May 10, 2018.

(51) Int. Cl.

| | |
|---|---|
| *C07K 1/30* | (2006.01) |
| *C07K 14/47* | (2006.01) |
| *C07K 1/36* | (2006.01) |
| *G01N 33/68* | (2006.01) |
| *C12N 15/70* | (2006.01) |

(52) U.S. Cl.
CPC .............. *C07K 1/303* (2013.01); *C07K 1/36* (2013.01); *C07K 14/47* (2013.01); *C12N 15/70* (2013.01); *G01N 33/68* (2013.01); *G01N 2800/2835* (2013.01)

(58) Field of Classification Search
None
See application file for complete search history.

(56) References Cited

FOREIGN PATENT DOCUMENTS

| | | |
|---|---|---|
| WO | 2012/061788 A2 | 5/2012 |
| WO | 2012/061789 A1 | 5/2012 |

OTHER PUBLICATIONS

Wang et al., Supplemental Figures PDF printout associated with PNAS 108: 43 pp. 17797-17802 (IDS document). Downloaded Jul. 30, 2022 (Year: 2011).*
Eastwood and Mulvihill (Tim Bartels (ed.), Alpha-Synuclein: Methods in Molecular Biology, vol. 1948, Chapter 10, pp. 113-121; Available online Feb. 16, 2019 (Year: 2019).*
PDF Eastwood and Mulvihill cover sheet with Feb. 16, 2019 online availability. Downloaded Jul. 30, 2022. (Year: 2022).*
PDF Ammonium sulfate precipitation from Wikipedia. Downloaded on Jul. 30, 2022. (Year: 2022).*
Wang et al., "A soluble alpha-synuclein construct forms a dynamic tetramer", Sep. 19, 2011, PNAS vol. 108, No. 43, p. 17797-17802.
Trexler et al., "N-terminal acetylation is critical for forming alpha-helical oligomer of alpha-synuclein", Mar. 9, 2012, Protein Science vol. 21:601-605.

* cited by examiner

*Primary Examiner* — Anand U Desai
(74) *Attorney, Agent, or Firm* — WC&F IP

(57) ABSTRACT

Tetrameric N-terminally acetylated α-synuclein is prepared by transforming an expression system with an expression vector encoding α-synuclein, wherein the expression system expresses a native NatB acetylase complex or ortholog thereof and/or wherein an exogenous NatB acetylase complex or ortholog thereof is co-expressed in the expression system, inducing protein expression in the transformed expression system, lysing cells in the transformed expression system to produce a cell lysate, performing salt precipitation of the cell lysate, recovering tetrameric N-terminally acetylated α-synuclein by centrifugation, and purifying the tetrameric N-terminally acetylated α-synuclein. Compositions comprising the same and methods for identifying compounds that stabilize natively folded tetrameric α-synuclein are also provided.

12 Claims, 6 Drawing Sheets

Specification includes a Sequence Listing.

US 11,673,913 B2

PREPARATION OF RECOMBINANT TETRAMERIC N-ACETYLATED ALPHA-SYNUCLEIN

FIELD OF THE INVENTION

The invention is generally related to gentle methods for preparing tetrameric α-synuclein without the use of detergent additives, boiling, or acid treatments.

BACKGROUND OF THE INVENTION

The native folding preferences of α-synuclein (αS), a key protein implicated in Parkinson's disease (PD) pathogenesis, and the physiological relevance of its dynamic nature have intrigued both biophysicists and biochemists since its discovery, with new assembly patterns continuing to come out of the shadows.[1-8] αS has traditionally been described as a natively unfolded monomeric protein.[9] Monomeric αS is prone to aggregation into β-sheet fibrils that are found as a principal component of Lewy bodies, the histopathological hallmark of PD. However, recent studies have shown evidence for physiologically relevant multimers in vivo, including a complex folded tetrameric αS structure of 58 kDa in human erythrocytes, cultured neurons, and freshly biopsied human brain tissue.[10, 11] Unlike the intrinsically disordered αS monomer, tetrameric αS has substantial α-helical character and has been shown to be aggregation-resistant. Further studies have demonstrated the presence of both monomeric and tetrameric αS in variable amounts according to the origin of cell extraction, yet intact-cell crosslinking protocols are necessary to recover tetrameric αS from neurons following cell lysis.[12] These observations suggest a dynamic exchange between the two conformations. Moreover, the introduction of disease-relevant αS point mutations results in reduced tetramer and enhanced monomer levels in vivo, and this same trend has been definitively linked to neurotoxicity.[11] Cumulatively, these studies suggest that failure to maintain tetrameric αS, thus leading to a concomitant shift to monomeric αS, could represent a mechanism for disease initiation.

It has been proposed that the aggregation-resistance of the tetramer is central to maintaining neuronal homeostasis.[10, 11] Therefore, stabilizing the tetrameric αS structure may be a plausible strategy to hamper PD. Understanding the dynamic mechanism by which an unfolded monomer converts into the tetramer, and developing a blueprint of both assembly and disassembly, would induce potential development towards new pharmacotherapies based on tetramer stabilization.[11] Augmenting the fundamental understanding of tetrameric αS dynamics is essential to this goal, and these biochemical studies will require access to purified tetrameric αS. In humans, N-terminally acetylated αS ($^{NAc}$αS) is the native form, with an acetyl group installed on the free amine of the starting methionine residue as a post-translational modification (PTM).[13, 14] This PTM has been demonstrated to impact αS structural propensities and its interactions with relevant biomolecules.[15-19]

Recombinant tetrameric αS has been generated previously using a fusion protein platform, however this construct is not the native human sequence; it carries an additional 10 amino acid residues at the N-terminus which remain following cleavage from the linker region.[20] Moreover, both the fusion protein-derived αS variant and another report of recombinant (native) $^{NAc}$αS tetramer production[21] both explicitly require the nonionic detergent, N-Octyl-β-D-glucoside, to be present during lysis and all subsequent purification steps. The strict detergent requirement in these studies is notable since residual detergent may contribute to tetramer stability and would certainly complicate any downstream analysis of tetramer dynamics.

Therefore, methods for isolating tetrameric αS without the use of detergent additives are urgently needed.

SUMMARY OF THE INVENTION

An aspect of the present disclosure provides a method for preparing tetrameric N-terminally acetylated α-synuclein, comprising the steps of: transforming an expression system with an expression vector encoding α-synuclein, wherein the expression system expresses a native NatB acetylase complex or ortholog thereof and/or wherein an exogenous NatB acetylase complex or ortholog thereof is co-expressed in the expression system, inducing protein expression in the transformed expression system, lysing cells in the transformed expression system to produce a cell lysate, performing salt precipitation of the cell lysate, recovering tetrameric N-terminally acetylated α-synuclein by centrifugation, and purifying the tetrameric N-terminally acetylated α-synuclein.

In some embodiments, the expression system is *Escherichia coli*. In some embodiments, the acetylase complex is a *Schizosaccharomyces pombe* acetylase complex. In some embodiments, the cell lysate is brought to 25% saturation in a first phase of an ammonium sulfate precipitation and is brought to 50% saturation in a second phase of an ammonium sulfate precipitation. In some embodiments, the tetrameric N-terminally acetylated α-synuclein is recovered between 30-50% ammonium sulfate saturation. In some embodiments, the method is performed in the absence of detergent. In some embodiments, the method is performed in the absence of boiling or acid treatment. In some embodiments, the purifying step is performed by anion exchange chromatography followed by size exclusion chromatography. In some embodiments, pooled fractions recovered from size exclusion chromatography are used as input for a second size exclusion chromatography step. In some embodiments, the α-synuclein encoded by the expression vector has a sequence as provided in SEQ ID NO: 1

Another aspect of the present disclosure provides a composition comprising tetrameric N-terminally acetylated α-synuclein prepared by a method as disclosed herein.

Another aspect of the present disclosure provides a composition comprising tetrameric N-terminally acetylated α-synuclein at a concentration of at least 2 mg/L. In some embodiments, the concentration is at least 3 mg/L. In some embodiments, the purity level of the composition is at least 90%. In some embodiments, the composition is free of detergents.

Another aspect of the present disclosure provides a method for identifying compounds that stabilize natively folded tetrameric α-synuclein, comprising the steps of providing a composition comprising tetrameric α-synuclein prepared by a method as disclosed herein; contacting the composition with a test compound, wherein an unstable conformation of the tetrameric α-synuclein is induced either before, during, or after this step; incubating the composition with the test compound under suitable conditions and for a duration of time sufficient to observe a stabilizing effect; and determining the ratio of natively folded tetrameric α-synuclein to non-native state α-synuclein, wherein an increase in the ratio of natively folded tetrameric α-synuclein to non-native state α-synuclein in the presence of the test compound as compared to in the absence of the test compound indicates that the test compound stabilizes the natively folded tetrameric α-synuclein.

In some embodiments, the duration of time sufficient to observe a stabilizing effect is an amount of time required to induce conformational conversion of unstable tetrameric α-synuclein to stable tetrameric α-synuclein. In some embodiments, the unstable tetrameric α-synuclein is induced by a mutation. In some embodiments, the unstable tetrameric α-synuclein is induced by proteolysis. In some embodiments, the unstable tetrameric α-synuclein is induced by phosphorylation. In some embodiments, the unstable tetrameric α-synuclein is induced by a denaturant.

DETAILED DESCRIPTION

Figure 1:
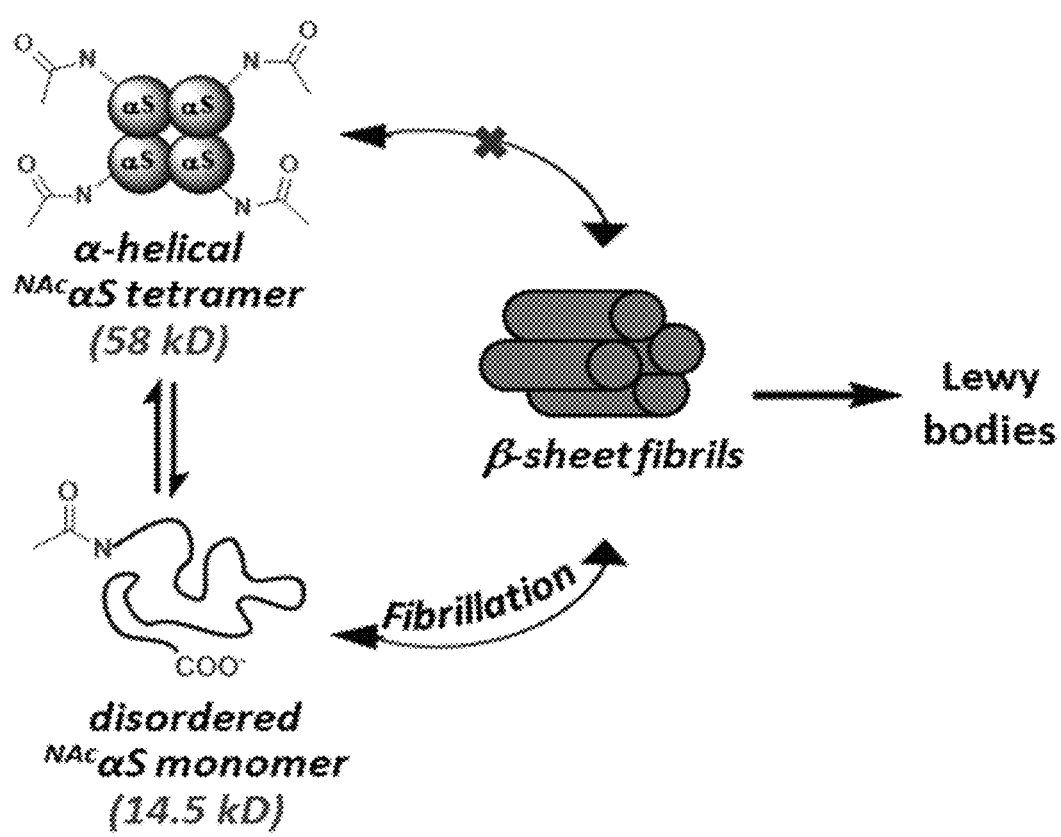
FIG. 1. Schematic representation of the dynamic nature of $^{NAc}$αS. $^{NAc}$αS exists as a folded aggregation resistant tetramer or a disordered monomer that can undergo fibrillation to produce β-sheet fibrils—a cardinal feature of Lewy bodies.

Described herein are methods for the preparation of recombinant native tetrameric N-acetylated α-synuclein ($^{NAc}$αS) without the use of detergents (such as β-D-glucopyranoside) or other structure-modifying additives which may alter protein conformation. To address concerns regarding tetramer stability and to provide a reliable source of natively folded tetrameric $^{NAc}$αS for systematic biochemical studies, a robust, mild, and detergent-free protocol for isolation of the elusive tetrameric conformer of $^{NAc}$αS is provided. The isolation methods may utilize gentle cell lysis conditions, a mild ammonium sulfate fractionation, and multiple chromatography steps performed at minimal system pressures.

The term "α-synuclein polypeptide" or "α-synuclein" as used herein refers to a polypeptide that shows a high degree of sequence identity with a wild type α-synuclein polypeptide such as, for example, wild type human α-synuclein. The wild-type, full-length form of human α-synuclein is a 140 amino acid polypeptide comprising the following amino acid sequence (see, for example, Accession Number: NP_000336.1): MDVFMKGLSK AKEGVVAAAE KTKQGVAEAA GKTKEGVLYV GSKTKEGVVH GVATVAEKTK EQVTNVGGAV VTGVTAVAQK TVEGAGSIAA ATGFVKKDQL GKNEEGAPQE GILEDMPVDP DNEAYEMPSE EGYQDYEPEA (SEQ ID NO: 1).

In some embodiments, an α-synuclein polypeptide as described herein shows at least 75%, 80%, 85%, 90%, 91%, 92%, 93%, 94%, 95%, 96%, 97%, 98%, 99% or 100% overall sequence identity with SEQ ID NO:1. In some embodiments, the identical residues are contiguous. In some embodiments, an α-synuclein polypeptide may include one or more point mutations as compared with SEQ ID NO:1 that are associated with a disease, disorder or condition. For example, certain monogenic point mutations, including but not limited to A30P, A53T, and E46K, have been identified as causal factors of early onset familial Parkinson disease.

As used herein, "an expression vector encoding α-synuclein" refers to an expression vector encoding any α-synuclein polypeptide as described herein which includes but is not limited to wild-type α-synuclein, a polypeptide comprising SEQ ID NO: 1, a polypeptide having at least 75% sequence identity to SEQ ID NO: 1 (the sequence identity may or may not be contiguous), and a mutant or variant α-synuclein.

As used herein, "natively folded tetrameric α-synuclein" refers to the native conformation of a stable complex comprised of four α-synuclein polypeptides. The natively folded stable complex of α-synuclein may be resistant to degradation and/or aggregation.

The term "isolated," as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, at least about 20%, at least about 30%, at least about 40%, at least about 50%, at least about 60%, at least about 70%, at least about 80%, at least about 90%, or more of the other components with which they were initially associated. In some embodiments, isolated agents are more than 90%, 91%, 92%, 93%, 94%, 95%, 96%, 97%, 98%, 99% pure.

"Purified" or "to purify" refers to removal of undesired components, e.g. contaminating proteins or other organic molecules, from a sample thereby increasing the percentage of the desired protein. The terms "modified", "mutant" or "variant" are used interchangeably herein, and refer to: (a) a nucleotide sequence in which one or more nucleotides have been added or deleted, or substituted with different nucleotides or modified bases or to (b) a protein, peptide or polypeptide in which one or more amino acids have been added or deleted, or substituted with a different amino acid. A variant may be naturally occurring, or may be created experimentally by one skilled in the art. A variant may be a protein, peptide, polypeptide or polynucleotide that differs (i.e., an addition, deletion or substitution) in one or more amino acids or nucleotides from the parent sequence.

Some embodiments of the disclosure provide a method for preparing tetrameric N-terminally acetylated α-synuclein, comprising the steps of: transforming an expression system with an expression vector encoding α-synuclein, wherein the expression system expresses a native NatB acetylase complex or ortholog thereof and/or wherein an exogenous NatB acetylase complex or ortholog thereof is co-expressed in the expression system, inducing protein expression in the transformed expression system, lysing cells in the transformed expression system to produce a cell lysate, performing salt precipitation of the cell lysate, recovering tetrameric α-synuclein by centrifugation, and and purifying the tetrameric N-terminally acetylated α-synuclein. If an exogenous NatB acetylase complex or ortholog thereof is expressed in the expression system, the expression vector encoding the acetylase complex may be the same or different as the expression vector encoding α-synuclein.

In some embodiments, the expression system is a bacterial expression system. In some embodiments, the bacterial expression system is *Escherichia coli*, for example BL21 (DE3) cells. Other suitable bacterial expression systems are known in the art and include, but are not limited to, *Bacillus subtilis*, *Pseudominonas fluorescens*, *Corynebacterium*, *Lactococcus lactis*, and *Streptomyces lividans* strains. Suitable eukaryotic expression systems include, but are not limited to, *Pichia pastoris* (yeast), *Saccharomyces cerevisiae* (yeast), *Schizosaccharomyces pombe* (yeast), *Trichoderma reesei* (filamentous fungi), and *Aspergillus oryzae* (filamentous fungi). Other suitable expression systems include, but are not limited to mammalian systems (e.g. CHO, HEK293, etc.) and baculoviral/insect cell systems (e.g. Sf-9, Sf-21, etc.).

The acetylase complex may be derived from any suitable source. In some embodiments, the acetylase complex is an N-terminal acetyltransferase B (NatB) enzyme or an ortholog thereof. NatB enzymes and orthologs thereof are highly conserved in eukaryotes and comprise a catalytic subunit (Naa20 or an ortholog thereof) and a regulatory subunit (Naa25 or an ortholog thereof). In some embodiments, the acetylase complex is a *Schizosaccharomyces pombe* acetylase complex, for example, having a Naa20 subunit sequence as set forth in SEQ ID NO: 2 and a Naa25 sequence as set forth in SEQ ID NO: 3. In some embodiments, the acetylase complex comprises subunits having at least 50%, 55%, 60%, 65%, 70%, 75%, 80%, 85%, 90%, 91%, 92%, 93%, 94%, 95%, 96%, 97%, 98%, 99% or 100% overall sequence identity with SEQ ID NO: 2 and SEQ ID NO: 3. The NatB complex recognizes and acetylates proteins that begin with a methionine followed by an aspartate. Expression of the acetylase complex allows for the addition of an acetyl group on the free amine of the starting methionine residue of α-synuclein. This post-translational modification mimics the native form of α-synuclein.

The term "expression vector" refers to a recombinant DNA molecule containing the appropriate control nucleotide sequences (e.g., promoters, enhancers, repressors, operator sequences and ribosome binding sites) necessary for the expression of an operably linked nucleotide sequence in a particular host cell. Thus, the expression vector is host-specific. The expression vector may be self-replicating, such as a plasmid, and may therefore carry a replication site, or it may be a vector that integrates into a host chromosome either randomly or at a targeted site. The expression vector may contain a selection gene as a selectable marker for providing phenotypic selection in transformed cells. The expression vector may also contain sequences that are useful for the control of translation.

The term "ortholog" refers to genes in different species that evolved from a common ancestral gene by speciation. "Homologous sequences" or "homologs" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pa.). Other non-limiting alignment programs include Sequencher (Gene Codes, Ann Arbor, Mich.), AlignX, and Vector NTI (Invitrogen, Carlsbad, Calif.).

The term "operably linked/linking" refers to a nucleotide sequence positioned relative to the control nucleotide sequences to initiate, regulate or otherwise direct transcription and/or the synthesis of the desired protein molecule.

A nucleotide sequence "encodes" or "codes for" a protein if the nucleotide sequence can be translated to the amino acid sequence of the protein. The nucleotide sequence may or may not contain an actual translation start codon or termination codon.

Induction of protein expression in the transformed bacterial expression system may be performed by methods known in the art, such as the addition of Isopropyl β-D-1-thiogalactopyranoside (IPTG), lactose, arabinose, rhamnose, proprionate, galactose, phosphate, copper, tetracycline, and ponasterone A. As is known in the art, the selection of a suitable inducer will depend on the promoter used in the expression vector and the host organism machinery (native or engineered).

Gentle methods of cell lysis, e.g. as described in the Example, are preferred. For example, the cells may be suspended in a detergent-free lysis buffer optionally supplemented with a protease inhibitor such as phenylmethylsulfonyl fluoride (PMSF). The cells may be physically lysed, e.g. via a sonicator, while being kept cold, e.g. 4° C. or lower. Other suitable cell lysis methods include mechanical disruption, liquid homogenization, and freeze-thaw methods. Any or all steps of cell lysis including centrifugation to remove cellular debris after cell lysis may may be performed in the cold, e.g. at 4° C. or lower.

Salt precipitation or fractionation may be used to separate proteins by altering their solubility in the presence of a high salt concentration. Suitable salts include, but are not limited to, ammonium sulfate and sodium or potassium chloride. Ammonium sulfate is especially useful as a precipitant because it is highly soluble, stabilizes protein structure, has a relatively low density, is readily available, and is relatively inexpensive. The solubility of proteins varies according to the ionic strength of the solution, thus according to the salt concentration. At low ion concentrations (<0.5 M), the solubility of proteins increases with increasing salt concentration, an effect termed "salting in". As the salt concentration is further increased, the solubility of the protein begins to decrease. At a sufficiently high ionic strength, the protein will precipitate out of the solution, an effect termed "salting out". When the ammonium ($NH_4^+$) and sulfate ($SO_4^{2-}$) ions are within the aqueous solution they are attracted to the opposite charges evident on the compound that is being purified. This attraction of opposite charges prevents the water molecules from interacting with the compound being purified, leading to the precipitation or "salting out". In some embodiments, an organic cosolvent is added to a primary solvent to increase solubility.

Tetrameric α-synuclein may generally be isolated between 30-50% ammonium sulfate saturation inclusive. In some embodiments, ammonium sulfate precipitation involves a single step of saturation within the range of 30-50% to precipitate the tetrameric α-synuclein. In some embodiments, ammonium sulfate precipitation involves two or more steps of saturation. For example, the cell lysate may be brought to 1-30% saturation, e.g. 25% saturation in a first phase in order to precipitate out contaminating proteins which are then removed by centrifugation. The cell lysate may then be brought to saturation within 30-50% or higher in a second phase in order to precipitate the tetrameric α-synuclein.

Once tetrameric α-synuclein has been precipitated, it may be further purified (i.e. separated from other precipitated proteins) by using one or more chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through".

In ion exchange chromatography, charged patches on the surface of the solute are attracted by opposite charges attached to a chromatography matrix, provided the ionic strength of the surrounding buffer is low. Elution is generally achieved by increasing the ionic strength (i.e. conductivity) of the buffer to compete with the solute for the charged sites of the ion exchange matrix. Common matrices are cellulose, agarose, polymethacrylate, polystyrene, and polyacrylamide. Changing the pH and thereby altering the charge of the solute is another way to achieve elution of the solute. The change in conductivity or pH may be gradual (gradient elution) or stepwise (step elution). In the past, these changes have been progressive; i.e., the pH or conductivity is increased or decreased in a single direction. In some embodiments, the tetrameric α-synuclein is purified by anion exchange chromatography in which the stationary phase is positively charged.

The flow rate for ion exchange chromatography refers to how fast buffer is being passed over a resin. The flow rate therefore determines the amount of time in which proteins can interact with the column resin, which is called the residence time. Flow rate can affect both resolution and capacity. Although slower flow rates may provide better resolution and capacity, this is often at the expense of protein activity. In some embodiments of the present disclosure, the flow rate used for ion exchange chromatography is about 2 mL/min or less, e.g. 1.5 mL/min or 1.0 mL/min or less. In some embodiments, the pressure is maintained at 0.5 MPa or lower, e.g. 0.3 MPa or 0.15 MPa or lower.

In size exclusion chromatography, molecules are separated by their size or molecular weight. The chromatography column is packed with fine, porous beads which are composed of dextran polymers (Sephadex), agarose (Sepharose), or polyacrylamide (Sephacryl or BioGel P). The pore sizes of these beads are used to estimate the dimensions of macromolecules. Size exclusion chromatography may be used for fractionation or desalting (or buffer exchange).

For size exclusion chromatography, moderate flow rates typically offer better resolution. Flow rates that are too slow may reduce resolution since the peaks or bands may diffuse too much as they travel through the column. In some embodiments of the present disclosure, the flow rate used for size exclusion chromatography is about 1 mL/min or less, e.g. 0.75 mL/min or 0.5 mL/min or less. In some embodiments, the pressure is maintained at 0.15 MPa or lower, e.g. 0.1 MPa or 0.05 MPa or lower.

Tetrameric α-synuclein may be purified by any suitable chromatographic method. In some embodiments, only anion-exchange chromatography or only size exclusion chromatography is used. In some embodiments, both anion-exchange chromatography and size exclusion chromatography are used in any order. In some embodiments, pooled fractions recovered from size exclusion chromatography are used as input for at least a second size exclusion chromatography step.

Embodiments of the disclosure also provide compositions comprising tetrameric N-terminally acetylated α-synuclein prepared by methods as disclosed herein. In some embodiments, the concentration of tetrameric N-terminally acetylated α-synuclein in the composition is at least about 1 mg/L, e.g. about 1.5 mg/L, 2 mg/L, 2.5 mg/L, 3 mg/L, 3.5 mg/L, 4 mg/L or more. In some embodiments, the composition is free of detergents, such as β-D-glucopyranoside (BOG). In some embodiments, the composition comprising tetrameric N-terminally acetylated α-synuclein is more than 70%, e.g. more than 80%, e.g. more than 90%, 91%, 92%, 93%, 94%, 95%, 96%, 97%, 98%, 99% pure.

Tetrameric α-synuclein has been suggested as a drug target for Parkinson's disease, Lewy body dementia, and other synucleinopathies. Parkinson's disease is multifactorial, likely resulting from an intricate relationship of genetic and environmental factors affecting fundamental cellular processes. Histopathological hallmarks of Parkinson's disease include the development of granular inclusions known as Lewy bodies that are enriched with aggregates of the protein α-synuclein (FIG. 1). Historically, αS has been considered a natively unfolded protein prone to amyloidogenic behavior. However, recent studies have revealed a physiologically relevant folded αS tetramer that is both alpha-helical and aggregation-resistant. The two forms are thought to reside in a dynamic coexistence within cells, and it has been suggested that a shift from metastable tetramers to the monomeric form could serve as a mechanism for disease initiation.

The present disclosure provides methods for identifying, detecting, and/or characterizing α-synuclein regulators. For example, the disclosure provides methods for identifying and/or characterizing agents that stabilize natively folded tetrametic α-synuclein. Such methods may comprise steps of: (a) providing a composition comprising tetrameric α-synuclein prepared by a method according to claim 1; (b) contacting the composition with a test compound, wherein an unstable conformation of the tetrameric α-synuclein is induced either before, during, or after step (b); (c) incubating the composition with the test compound under suitable conditions and for a duration of time sufficient to observe a stabilizing effect; and (d) determining the ratio of natively folded tetrameric α-synuclein to non-native state α-synuclein, wherein an increase in the ratio of natively folded tetrameric α-synuclein to non-native state α-synuclein in the presence of the test compound as compared to in the absence of the test compound indicates that the test compound stabilizes the natively folded tetrameric α-synuclein. In some embodiments, the duration of time sufficient to observe a stabilizing effect is an amount of time required to induce conformational conversion of unstable tetrameric α-synuclein to stable tetrameric α-synuclein.

In some embodiments, such methods involve testing of a variety of test compounds, for their ability to regulate the stability (e.g., stabilize or destabilize) of α-synuclein tetramer, thereby new regulators are identified or detected. In some embodiments, such methods involve testing a known or suspected regulator. In some embodiments, such regulators may affect the formation of α-synuclein tetramer complex. In some embodiments, such regulators may affect the maintenance of existing α-synuclein tetramer complex.

In some embodiments, provided methods include steps of determining a ratio of tetrameric α-synuclein to non-native state α-synuclein. When an increase in the ratio of natively folded tetrameric α-synuclein to non-native state α-synuclein in the presence of an agent is observed, as compared to in the absence of the agent, this observation indicates that the agent stabilizes tetrameric α-synuclein; the agent is therefore identified and/or characterized as a stabilizer of tetrameric α-synuclein. Converse findings identify and/or characterize the agent as a destabilizer of tetrameric α-synuclein.

In some embodiments, agent and sample are contacted in the presence of one or more denaturants. Typically, a denaturant may be added to induce a certain degree of "stress" to the tetrameric α-synuclein in a reaction in a controlled fashion. Such embodiments provide information about ability of an agent to effectively resist denaturant effects over time, or in some cases correct the denaturing effect of the denaturant. In some embodiments, tetramer stabilizing activity of an agent in the presence of a denaturant restores conformation of one or more α-synuclein polypeptides and/or tetramers. For example, in some embodiments, an agent helps restore the native conformation of the tetrameric α-synuclein by converting a mis-folded complex into a correctly folded complex. Suitable denaturants may include but are not limited to acid, base, high salt, low salt, heat, etc.

In some embodiments, assays may be carried out using tetrameric α-synuclein that is not folded correctly. For example, at least one of the α-synuclein polypeptides may contain at least one point mutation, which can affect the folding of the protein and the subsequent complex formation of tetramer. In some embodiments, at least one of the α-synuclein polypeptides may contain a truncated form of α-synuclein caused by proteolysis, which results in unstable tetrameric α-synuclein. Using unstable or mis-folded tetrameric α-synuclein, one of ordinary skill in the art may identify compounds that can stabilize and/or correct the conformation of the misfolded complex. In certain embodiments, α-synuclein may form monomer, dimer, trimer, as well as larger multimers, etc., which are more prone to resulting in toxic aggregates. The present disclosure also embraces methods for identifying compounds that can bind to and stabilize such abnormal counterparts of α-synuclein oligomers, which then can prevent these species from forming toxic aggregates in cells.

In some embodiments, natively folded tetrameric α-synuclein is comprised of wild-type full-length α-synuclein and is capable of forming stable tetramer with native conformation. Certain factors, including but not limited to genetic and/or environmental factors, may affect the conformation and/or stability of tetrameric α-synuclein. For example, at least one of the tetrameric α-synuclein polypeptides may contain at least one mutation (e.g., point mutations), which may cause distortion to the tetrameric conformation and/or may affect the stability of such a complex. It is contemplated that at least in some cases such mutations may contribute to the pathogenesis of a disease or disorder associated with abnormal α-synuclein function/expression. It is known, for example, that certain point mutations to α-synuclein, such as A30P, A53T and E46K, are causally associated with forms of Parkinson's disease. Accordingly, the present disclosure contemplates stabilizing native conformation α-synuclein using a compound that is a stabilizer of tetrameric α-synuclein. Thus, in some instances, such stabilizers may be used to stabilize natively folded (e.g., correctly folded) tetramer so as to maintain the conformation. Stabilizers used in this way may prevent an α-synuclein-associated disease or disorder. In some embodiments, however, a compound that is a stabilizer of natively folded tetrameric α-synuclein may also be used to "correct" certain mis-folding of tetrameric α-synuclein, which, for example, contains a point mutation, and therefore is more prone to mis-folding. When such a stabilizer is used in this way, the stabilizer may be effective as a therapeutic for a subject with genetic or environmental disposition for the pathogenesis of any one of α-synuclein-associated diseases or disorders. Thus, the present disclosure contemplates stabilizers of natively folded tetrameric a-synuclein which are useful for the prevention and/or treatment of α-synuclein-associated diseases or disorders.

Compounds to be screened, identified, and/or characterized using one or more methods described herein can be of any of a variety of chemical classes. In some embodiments, such compounds are small organic molecules having a molecular weight in the range of about 50 to about 2,500 daltons (Da). Such compounds can comprise functional groups involved in structural interaction with proteins (e.g., hydrogen bonding), and typically include at least an amine, carbonyl, hydroxyl, or carboxyl group, and preferably at least two such functional chemical groups. Such compounds often comprise cyclical carbon or heterocyclic structures and/or aromatic or polyaromatic structures (e.g., purine core) substituted with one or more of the above functional groups.

In some embodiments, compounds can be biomolecules such as, for example, polypeptides, peptidomimetics (e.g., peptoids), amino acids, amino acid analogs, saccharides, fatty acids, steroids, purines, pyrimidines, derivatives or structural analogues thereof, polynucleotides, nucleic acid aptamers, polynucleotide analogs, carbohydrates, lipids, etc., or combinations thereof.

Compounds can be obtained or provided from any of a number of potential sources, including: chemical libraries, natural product libraries, and combinatorial libraries comprised of random peptides, oligonucleotides, or organic molecules. Chemical libraries consist of diverse chemical structures, some of which are analogs of known compounds or analogs or compounds that have been identified as "hits" or "leads" in other drug discovery screens, while others are derived from natural products, and still others arise from non-directed synthetic organic chemistry. Natural product libraries are collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed or large numbers of peptides, oligonucleotides, or organic compounds as a mixture. These libraries are relatively easy to prepare by traditional automated synthesis methods, PCR, cloning, or proprietary synthetic methods. Still other libraries of interest include peptide, protein, peptidomimetic, multiparallel synthetic collection, recombinatorial, and polypeptide libraries. In some embodiments, a chemical "library" contains only compounds that are structurally related to one another (e.g., share at least one common structural moiety; in many embodiments, a common core). In some embodiments, a chemical "library" contains a plurality, and in some embodiments, a majority of compounds that are structurally related. In some embodiments, a chemical "library" contains a least one compound that is not structurally related (or not structurally significantly related) to other compounds in the library. For a review of combinatorial chemistry and libraries created therefrom, see Myers, Curr. Opin. Biotechnol. 8:701-707 (1997).

Compounds for use in accordance with the present invention can be synthesized by any chemical or biological method. The compounds identified above can also be pure, or may be in a heterologous composition (e.g., a pharmaceutical composition), and can be prepared in an assay-, physiologic-, or pharmaceutically-acceptable diluent or carrier.

The disclosure provides several screening methods to identify agents having a pharmacological activity useful in treating a synucleinopathy. The methods include screens that can be performed in vitro, in cells or transgenic animals, and which test a variety of parameters as an indication of activity. Agents determined to have an activity in these screens can be retested in secondary screens of animal models of synucleinopathy or in clinical trials to determine activity against behavioral or other symptoms of these diseases.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

1. Summary

In this Example, the first isolation of recombinant native tetrameric $^{NAc}\alpha S$ without the use of detergent additives during purification is described. Recombinant tetrameric $\alpha S$ has been generated previously using a fusion protein platform, however this construct is not the native human sequence; it carries an additional 10 amino acid residues at the N-terminus which remain following cleavage from the linker region.[20] Moreover, both the fusion protein-derived $\alpha S$ variant and another report of recombinant (native)$^{NAc}\alpha S$ tetramer production[21] both explicitly require the detergent n-octyl-β-D-glucoside (BOG) to be present during lysis and all subsequent purification steps. The strict BOG requirement in these studies is notable since disordered monomeric $\alpha S$ is known to become α-helical upon exposure to small unilamellar vesicles, including nonionic and electrostatically charged vesicles or detergents.[22-24] Accordingly, residual BOG may contribute to tetramer stability and would certainly complicate any downstream analyses of tetramer dynamics.

To address these concerns and to provide a reliable source of native tetrameric $^{NAc}\alpha S$ for systematic biochemical studies, provided herein is a robust, mild, and detergent-free protocol for isolation of the elusive tetrameric conformer of $^{NAc}\alpha S$.

2. Materials and Methods 2.1 Recombinant Heterologous Expression of N-Acetylated α-Synuclein ($^{NAc}\alpha S$)

Chemically competent *Escherichia coli* BL21 (DE3) cells were co-transformed with pET-αS, a pET-based plasmid carrying the SNCA gene (Accession AAH13293.1) which codes for wild type human αS protein, and pNatB (pACYC-duet-naa20-naa25), which codes for a fission yeast acetylase complex (NatB; Addgene plasmid #53613)[25] that can N-terminally acetylate αS in situ to provide $^{NAc}\alpha S$. A glycerol stock of the co-transformed strain was generated and stored at −80° C. This glycerol stock was used to inoculate a seed culture in 2×YT media supplemented with 25 μg/mL chloramphenicol and 30 μg/mL kanamycin, which was incubated with shaking (300 rpm) at 37° C. for 16 hours. This seed culture was then used to inoculate an expression culture (1 L of 2×YT media supplemented with 25 μg/mL chloramphenicol and 30 μg/mL kanamycin) which was incubated with shaking (300 rpm) at 37° C. until it reached an $OD_{600}$ of 0.6, at which point protein expression was induced with 1 mM isopropyl β-D-1-thiogalactopyranoside (IPTG) and incubated with shaking for an additional 4 hours. After incubation, the culture was pelleted in 400 mL batches by centrifuging at 5,000 rpm and 4° C. for 20 min. The supernatant was discarded, and the pellet was stored at −20° C.

2.2 Partial Purification of Tetrameric $^{NAc}\alpha S$

A cell pellet (~2 g from 400 mL culture) containing $^{NAc}\alpha S$ was resuspended in 25 mL lysis buffer (1 M Tris, 50 mM NaCl, 1 mM EDTA, pH 8.2) supplemented with 125 μL of 1 mM phenylmethylsulfonyl fluoride (PMSF). The cell suspension was lysed using a QSonica sonicator with a 3.2 mm (⅛") microtip probe (10 second on/off intervals; 3 min 20 sec total time; 20% amplitude) while kept cold in an ice bath. Cellular debris was removed by centrifugation at 20,000×g at 4° C. for 20 min. The cleared lysate was then enriched using a two-phase ammonium sulfate (($NH_4)_2SO_4$) fractionation process. The lysate was brought to 25% saturation (calculations were facilitated through the online ammonium sulfate calculator provided by EnCor Biotechnology Inc., (encorbio.com/protocols/AM-SO4.htm) and equilibrated in an ice bath with shaking motion for 1 hour. Precipitated proteins were removed by centrifugation again at 20,000×g at 4° C. for 20 min. The supernatant was collected and saturated to 50% $(NH_4)_2SO_4$, then equilibrated again while shaking in an ice bath for 1 hour; precipitated protein was pelleted using the same centrifugation parameters. $^{NAc}\alpha S$ precipitated between 30-50% $(NH_4)_2SO_4$ saturation as confirmed by SDS-PAGE electrophoresis (vide infra). Accordingly, the supernatant was discarded, and the enriched pellet was washed once with chilled $dH_2O$ and stored at −20° C. for future purification.

2.3 Anion Exchange Chromatography

The $(NH_4)_2SO_4$ pellet containing $^{NAc}\alpha S$ was resuspended in 10 mL of HiTrap® start buffer (20 mM tris, 25 mM NaCl, pH 8.0) and loaded onto an ÄKTA Start FPLC system fitted with a HiTrap® Q HP anion exchange column. For protein elution, we used HiTrap® start buffer as starting buffer and 20 mM Tris, 1 M NaCl, pH 8.0 as elution buffer, with a 1 mL/min flow rate. Tetrameric and monomeric $^{NAc}\alpha S$ co-eluted between 30-45% of elution buffer. Fractions containing $^{NAc}CS$ were pooled together and concentrated in a 3K centrifugal filter (Microsep™ Advance, Pall Corporation) at 5,000 rpm and 4° C.

2.4 Size Exclusion Chromatography (SEC)

The ÄKTA Start FPLC was fitted with a HiPrep™ 16/60 Sephacryl S-200-HR column for size exclusion chromatography. The pooled and concentrated $^{NAc}\alpha S$ sample was loaded onto the Sephacryl column, and SEC was performed at a flow rate of 0.5 mL/min with an elution buffer consisting of 20 mM Tris, 20 mM NaCl, pH 8.0. Protein elution was monitored by the UV/vis detector of the FPLC (280 nm), and fractions were evaluated by CD spectroscopy and SDS-PAGE analysis.

2.5 Circular Dichroism (CD) Spectroscopy

CD spectroscopy was performed on a JASCO J-1500 spectrophotometer. Samples were aliquoted into a 1 mm rectangular spectrophotometer cell (Starna), and spectra were acquired with a scanning range of 200-250 nm, a 0.5 nm data pitch, and a scan speed of 100 nm/min.

2.6 SDS-PAGE

During each purification step, a 100 μL aliquot was removed from the bulk sample and centrifuged at 8,000×g at 4° C. for 5 min. The supernatant was segregated from the pellet. Pellets were resuspended in 100 μL of 1×LDS sample buffer solution (CBS Scientific) with 1% dithiothreitol (DTT). For each of the supernatant samples, 13 μL was combined with 5 μL of 4×LDS sample buffer solution and 2.5 μL of 10% DTT. Sample (10 μL) was then loaded onto a 4-20% SDS-PAGE gel (ClearPAGE®, CBS Scientific). Gels were run at a constant voltage of 160 V for ~1 hour. Gels were stained with brilliant blue R-250 staining buffer, rinsed with $dH_2O$, and destained twice with destaining buffer (20% EtOH, 5% AcOH).

2.7 Blue Native (BN) Electrophoresis

Samples were prepared for Blue Native PAGE (BN-PAGE) using 4× RunBlue Native sample solution (CBS Scientific) and supplemented to a final concentration of 1% DTT. Prior to sample loading, the wells of a 4-16% bis-tris acrylamide gel (Invitrogen) were filled with BN-PAGE cathode buffer (500 mM 6-aminohexanoic acid, 25 mM imidazole, 0.02% G-250, pH 7.0). A 20 μL aliquot from each sample was loaded onto the gel. The inner chamber was filled with cathode buffer, whereas the outer chamber was filled with BN-PAGE anode buffer (25 mM imidazole, pH 7.0). The gel ran for 1 hour at a constant voltage of 160 V, then was paused for buffer exchange. The cathode buffer was removed from the inner chamber and was replaced with ¹⁄₁₀ cathode buffer containing a reduced concentration of the G-250 dye (500 mM 6-aminohexanoic acid, 25 mM imidazole, 0.002% G-250, pH 7.0). Electrophoresis was then resumed at a constant voltage of 200 V for an additional hour. After electrophoresis, the gel was carefully rinsed with $dH_2O$ and treated with strong destaining solution (40% methanol 10% acetic acid). The immersed gel was microwaved for 30 seconds and set in rocking motion for 30 min. The strong destaining solution was decanted, and the gel was then immersed in mild destaining solution (8% acetic acid). The gel was microwaved for 30 seconds and set in rocking motion overnight.

2.8 Dot Blot Immunoassay of Tetrameric $^{NAc}\alpha S$

A dry sheet of 20 μm nitrocellulose membrane (VWR) was dot blotted with 3 μL of protein sample and let dry to prevent droplet dilation. Dot blotting was repeated 4-6 more times to increase protein concentration on the targeted region. The membrane was enclosed in miniblot holder from a SNAP i.d.® Protein Detection System (EMD Millipore), and the holder was secured in a SNAP i.d.® frame and placed on the system. The membrane was soaked with 10-15 mL of blocking buffer (15 ml ddH$_2$O, 0.5% w/v Biorad blotting-grade nonfat dry milk) for 10 min. The blocking buffer was removed from the system by vacuum. With the vacuum on, 5 mL of PBS-T buffer (0.1 M Na$_2$HPO$_4$, 0.15 M NaCl, 0.5% v/v Tween-20, pH 7.2) was then used to rinse the membrane. After turning off the vacuum, the membrane was incubated with 5 mL of anti-α-syn 14H2L1 rabbit monoclonal antibody (Fisher, 1:500 v/v dilution in 10% v/v PBS-T buffer) for 10 min. The primary antibody solution was then vacuumed out from the system. With the vacuum on, 15 mL of PBS-T buffer was used to wash membrane four times. After turning off the vacuum, the membrane was incubated with 10 mL of goat anti-rabbit horseradish peroxidase conjugate as a secondary antibody (Fisher 31460, 1:2000 v/v dilution in 10% v/v PBS-T buffer) for 10 min. After vacuum removal of the secondary antibody, the membrane was washed with 15 mL of PBS-T three times and once with PBS buffer. The membrane was then removed from the system and resuspended in 5-10 mL of 1-Step TMB-Blotting Substrate solution (Thermo Scientific) until the signal developed.

2.9 Protein Quantification

For total protein quantification in solution, a Coomassie Plus Bradford Assay Kit (Thermo Scientific) was utilized. Calibrations were conducted by using a four-parameter (quadratic) curve with an $R^2$ value of 0.9905. Determination of tetramer/monomer ratios and purity assessments were completed by calculating pixel value statistics using ImageJ, an open source image processing program developed at the National Institutes of Health (imagej.nih.gov/).

2.10 Mass Spectrometric Confirmation of $^{NAc}\alpha S$

The 56 kD band was excised from a BN-PAGE gel of the tetrameric $^{NAc}\alpha S$ sample and divided into 1 mm segments to aid in digestion. Gel pieces were transferred to a siliconized tube and washed and destained in 200 μL 50% methanol overnight. The gel pieces were dehydrated in acetonitrile, rehydrated in 30 μL of 10 mM DTT in 0.1 M ammonium bicarbonate and reduced at room temperature for 0.5 h. The DTT solution was removed and the samples were alkylated in 30 μL 50 mM iodoacetamide in 0.1 M ammonium bicarbonate at room temperature for 0.5 h. The reagent was removed and the gel pieces were dehydrated in 100 μL acetonitrile. The acetonitrile was removed and the gel pieces were rehydrated in 100 μL 0.1 M ammonium bicarbonate. The pieces were dehydrated in 100 μL acetonitrile, the acetonitrile removed and the pieces were completely dried by vacuum centrifugation. The gel pieces were rehydrated in 20 ng/μL trypsin in 50 mM ammonium bicarbonate on ice for 10 min. Any excess trypsin solution was removed and 20 μL 50 mM ammonium bicarbonate added. The samples were digested overnight at 37° C., and the peptides formed from the digestion were extracted from the polyacrylamide in two 30 μL aliquots of 50% acetonitrile/5% formic acid. These extracts were combined and evaporated to 15 μL for MS analysis.

The samples were analyzed by a Waters Synapt G2Si mass spectrometer system with a nanospray ion source interfaced to a Waters M-Class C18 reversed-phase capillary column. The peptides were injected onto the trap and analytical columns, and the peptides were eluted from the column by an acetonitrile/0.1% formic acid gradient at a flow rate of 0.4 μL/min over 60 minutes. The nanospray ion source was operated at 3.5 kV. A lockspray compound was used to improve the mass accuracy of the analysis. The digests were analyzed using the double play capability of the instrument acquiring full scan mass spectra at low collision energy to determine peptide molecular weights and product ion spectra at high collision energy to determine amino acid sequence. This mode of analysis produces approximately 10000 CAD spectra of ions ranging in abundance over several orders of magnitude. Not all CAD spectra are derived from peptides. The data were analyzed by database searching using the PLGS search algorithm against Uniprot's Human database.

3. Results and Discussion

3.1 Heterologous Expression of N-Terminally Acetylated Native Human α-Synuclein ($^{NAc}\alpha S$)

Human αS has been established as acetylated at the N-terminus as a post-translational modification,[16] and this PTM clearly impacts αS structure and dynamics. N-terminal acetylation has been suggested to increase the transient helical propensity[26] and promote tetramer assembly,[21] and it also has an effect on metal binding sites.[7, 27-31] For example, through recombinant expression systems in which the protein is non-acetylated, the N-terminal free amine has acted as an anchoring site for copper.[32] Copper binding still occurs with N-terminal acetylation but the structure is altered.[29-31] N-terminal capping has also been demonstrated to affect the secondary structure of αS.[18-20, 33] The N-acetyl group attenuates the alpha-amino positive charge of αS, interacting favorably with the helix dipole moment, leading to elevated helical content within the N-terminus that is further stabilized by hydrogen bonding. It has been postulated that the helical tetramer conformationally stabilizes αS by burying hydrophobic surfaces, thus diminishing the aggregation propensity.[34] Notably, non-acetylated αS has been demonstrated to extinguish access to the tetrameric conformation, in turn favoring the monomeric αS conformer.[21] Accordingly, obtaining native human αS protein—including the N-terminal acetylation PTM—is a prerequisite to probing αS tetramer stability and dynamics as well as the impact of any downstream structural effectors.

*Escherichia coli* was used as the heterologous host because of the typically robust recombinant protein yields and the convenience of well-established protocols for transformation and orthogonal expression machinery. The wild type αS expression plasmid contains the native human αS coding sequence in a pET-based parent vector. Native *E. coli* biochemical pathways lack the machinery to install N-terminal acetyl groups on expressed proteins, so $^{NAc}\alpha S$ was generated by co-transforming the pET-αS plasmid with pNatB, a vector coding for the NatB acetylase complex from fission yeast.[25] Co-expression of human αS and the NatB complex in *E. coli* BL21 (DE3) proceeded smoothly at 37° C. following IPTG induction, giving excellent induction bands for $^{NAc}\alpha S$ under typical expression conditions. Cell pellets could be frozen and stored at −20° C. without compromising the functionality and nature of $^{NAc}\alpha S$.

3.2 Cell Lysis and α-Synuclein Enrichment

Traditional methods of purifying recombinant αS or $^{NAc}\alpha S$ monomers include rather harsh conditions (boiling and acid treatment) since the natively unfolded monomeric αS protein can withstand extreme conditions.[27, 28, 35-37]

Tetrameric $^{NAc}\alpha$S, on the other hand, has proven to be much more labile and generally requires chemical cross-linking to maintain its structure during cell lysis or "molecular-crowding" conditions that simulate an intracellular environment. [12] Accordingly, we aimed to employ only mild methods of cell lysis and protein enrichment in order to maintain as much tetrameric $^{NAc}\alpha$S as possible.

Figure 2A:
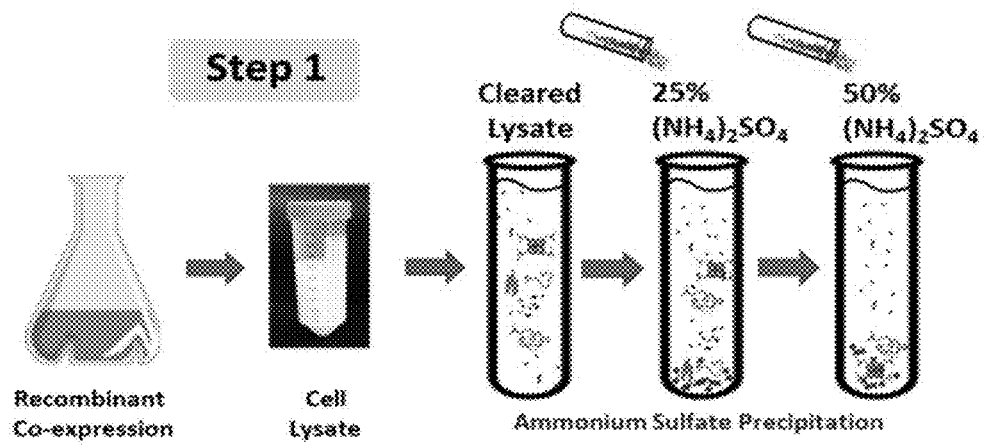
FIG. 2A-C. Cell lysis and partial purification of $^{NAc}$αS using mild conditions. (A) Cartoon representation of the first step of $^{NAc}$αS purification involving a two-phase ammonium sulfate precipitation; $^{NAc}$αS precipitates with 50% $(NH_4)_2SO_4$ supplementation. (B) Anion exchange chromatograph of the second step of $^{NAc}$αS purification; $^{NAc}$αS elutes within the 35-45% NaCl range. (C) SDS-PAGE analysis of the first two steps of $^{NAc}$αS purification; both monomeric and tetrameric conformers coelute from HiTrap® Q HP anion exchange column.
Figure 2B:
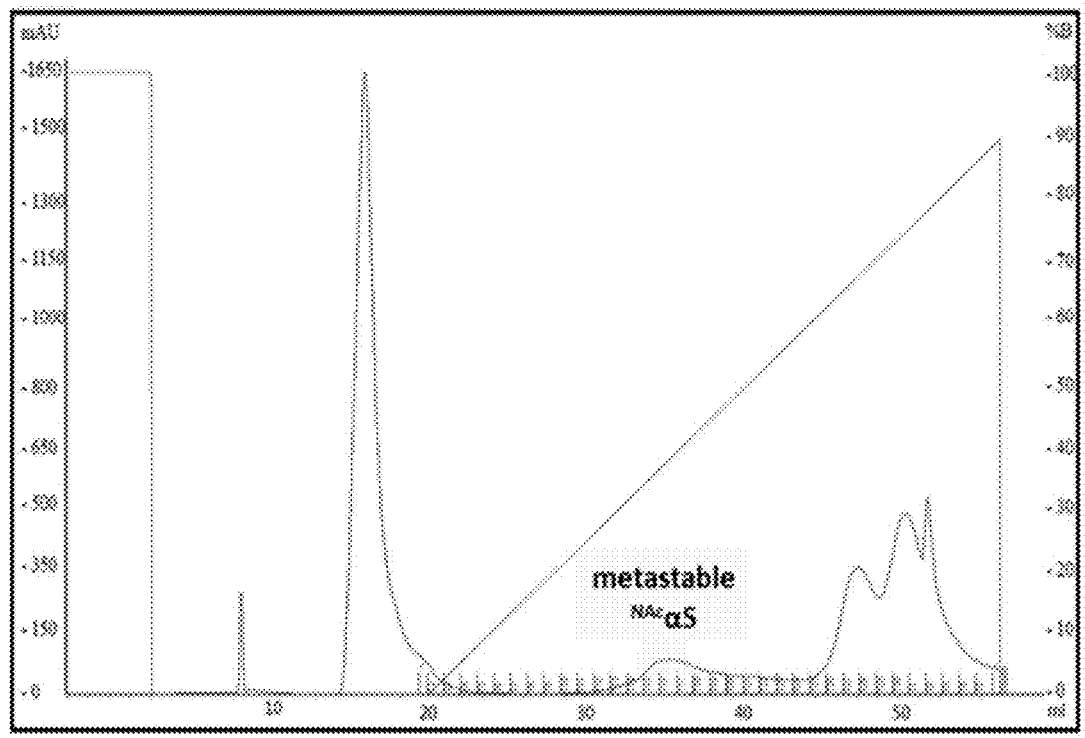
Figure 2C:
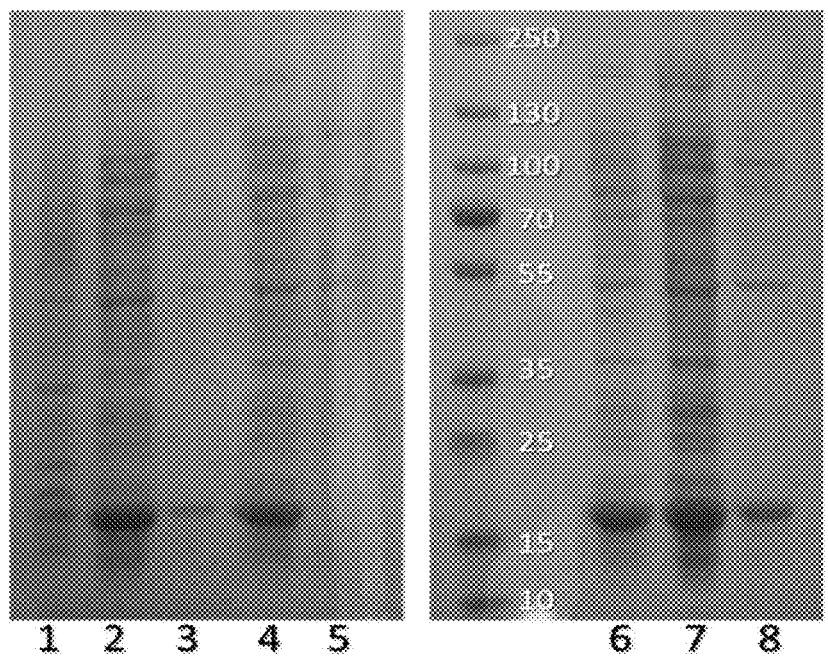
Figures 3A, 3B, 3C:
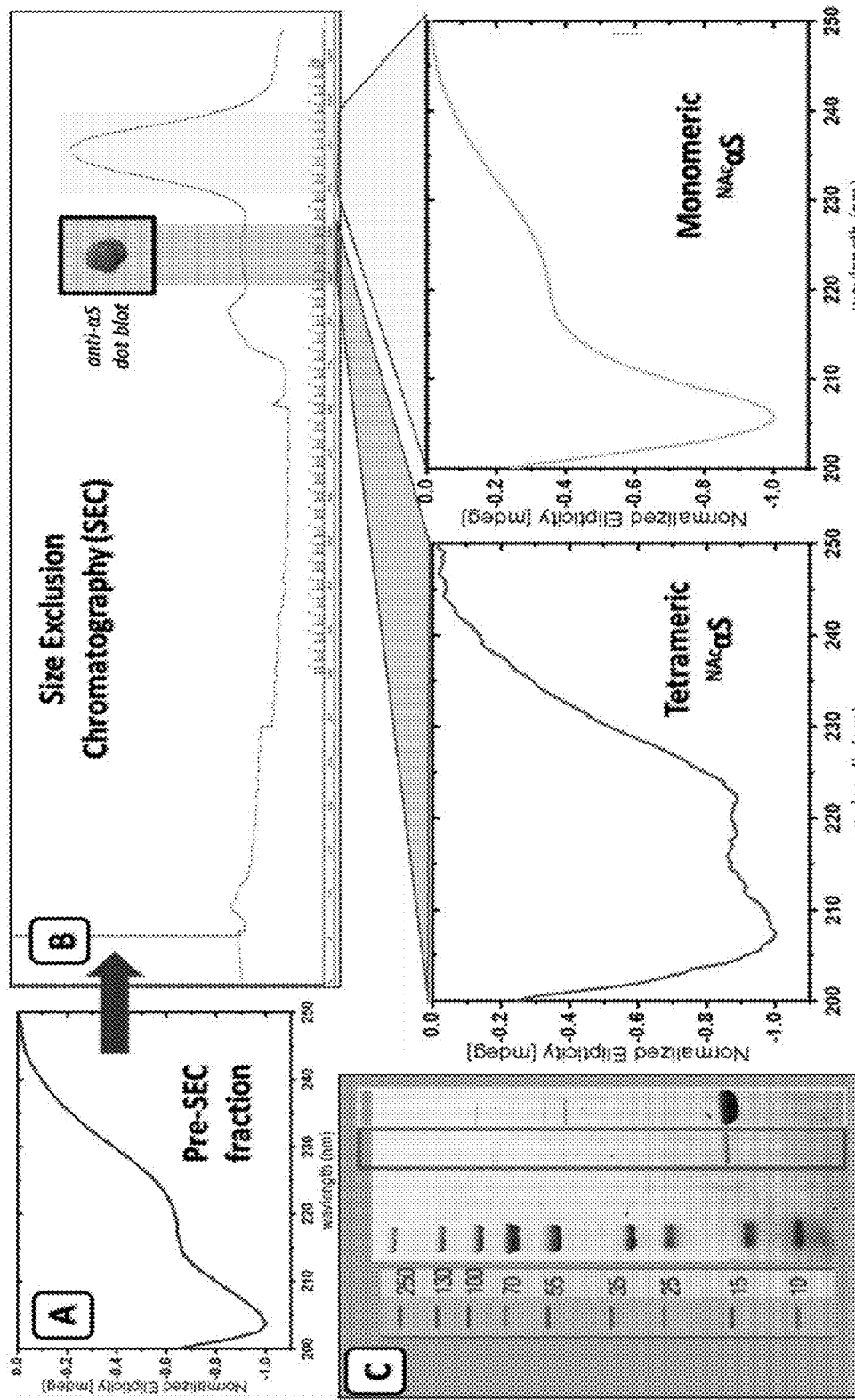
FIG. 3A-C. Separation of tetrameric and monomeric $^{NAc}$αS conformers by size exclusion chromatography (SEC). (A) Pre-SEC secondary structure characterization of metastable $^{NAc}$αS by CD spectroscopy following protein enrichment and concentration. (B) Size exclusion chromatograph with tetrameric and monomeric $^{NAc}$αS fractions highlighted. The post-SEC protein secondary structure demonstrate that the higher molecular weight fraction (tetrameric) is predominantly alpha-helical, while the lower molecular weight fraction (monomeric) is predominantly disordered. Inset: Dot blot using an anti-αS antibody that confirms the alpha-helical fraction as $^{NAc}$αS. (C) SDS-PAGE gel demonstrating the purity of tetrameric (left lane) and monomeric $^{NAc}$αS (right lane) following the third purification step of the protocol.

Following co-expression, we manually and gently resuspended the cell pellet into a standard lysis buffer to maintain reasonable ionic strength and pH. Once fully suspended, cells were lysed by probe sonication with a lowered amplitude (20%), being careful to keep the solution in an ice bath throughout. To preserve the fragile folding of tetrameric $^{NAc}$S, we strategized a two-step ammonium sulfate (($NH_4$)$_2SO_4$) fractionation process as a mild means of initial $^{NAc}\alpha$S enrichment. An initial saturation at 25% ($NH_4$)$_2SO_4$ removes some impurities, followed by precipitation of tetrameric $^{NAc}\alpha$S at 50% ($NH_4$)$_2SO_4$, as shown in FIG. 2. Once the targeted protein was successfully precipitated, we resuspended the ammonium sulfate pellet and began enriching the $^{NAc}\alpha$S tetramer through anionic exchange chromatography. A Hitrap® Q HP strong anion exchange column (GE Healthcare) was used on an ÄKTA start FPLC to elute the targeted protein at minimal pressures (max. 0.5 MPa) and flow rates ($\leq$1 mL/min). Metastable $^{NAc}\alpha$S (tetramer and monomer) is collected in fractions that elute between 30-45% of elution buffer, which is highlighted within the chromatogram shown in FIG. 2B. SDS-PAGE analysis following anionic exchange chromatography demonstrate a significant improvement in purity of metastable $^{NAc}\alpha$S (FIG. 2C). $^{NAc}\alpha$S fractions were then pooled and concentrated by centrifugal filtration using a 3 kD cutoff. Analysis of the secondary structural content of partially purified $^{NAc}\alpha$S by circular dichroism (CD) spectroscopy demonstrates both the alpha-helical and disordered nature of the protein ensemble (FIG. 3A).

3.3 Separation of Tetrameric $^{NAc}\alpha$S from the Monomeric Conformer

The enriched $^{NAc}\alpha$S ensemble was further purified by size exclusion chromatography (SEC), to separate tetrameric $^{NAc}\alpha$S from the monomeric form. The pooled and concentrated anion exchange fractions were analyzed by CD prior to injection onto the SEC column, and the spectrum suggested a mixture of both tetramer and monomer (FIG. 3A). This material was injected onto a HiPrep™ 16/60 Sephacryl S-200 HR (GE Healthcare) column. Two main peaks for $^{NAc}$As were observed, with the higher molecular weight tetramer eluting at ~85 mL and the lower molecular weight monomer eluting at ~95 mL (FIG. 3B). SDS-PAGE analysis of individual fractions verified that both main peaks contained $^{NAc}\alpha$S protein. To further elucidate the identity of $^{NAc}\alpha$S conformers within these peaks, each were characterized by CD spectroscopy in the 200-250 nm range (FIG. 3B). The higher molecular weight fraction displayed a spectrum consistent with an $\alpha$-helical structure, which is characteristic of tetrameric $^{NAc}\alpha$S. In contrast, the lower molecular weight fraction exhibited a spectrum that can be assigned to predominantly random coil, as is well-known for disordered monomeric $^{NAc}\alpha$S. To further verify that the alpha-helical CD signal derives from $^{NAc}\alpha$S, an anti-$\alpha$S (clone: 14H2L1) dot blot immunoassay was performed on SEC fractions collected from the higher molecular weight region to further confirm isolation of tetrameric $^{NAc}\alpha$S (FIG. 3B). SDS-PAGE analysis also confirmed $^{NAc}\alpha$S as the predominant protein within this fraction (FIG. 3C); the noncovalent tetramer runs at a molecular weight consistent with the monomer under denaturing conditions (vide infra).

3.4 Polishing of Purified Tetrameric $^{NAc}\alpha$S

Figures 4A, 4B, 4C:
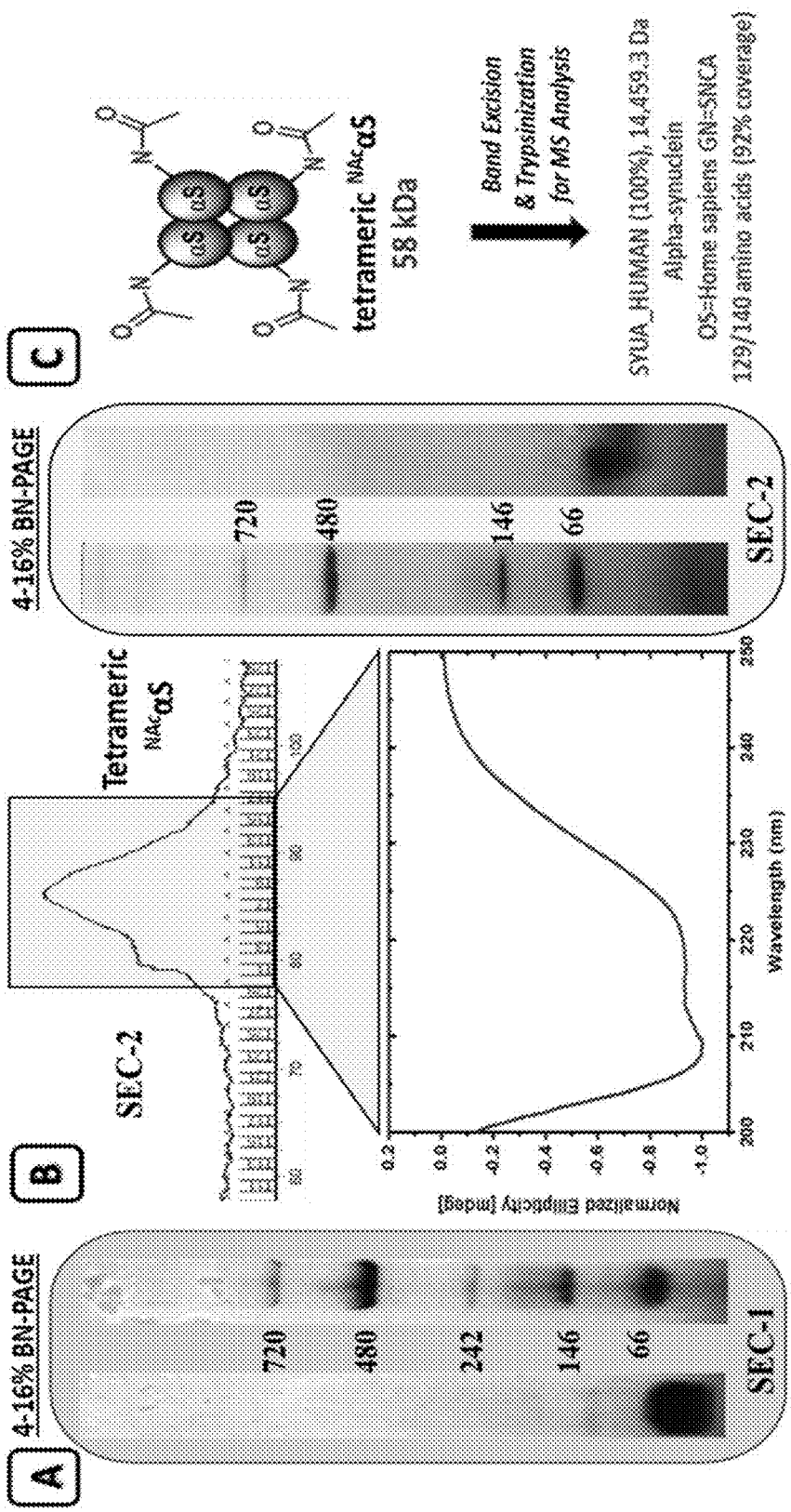
FIG. 4A-C. Polishing the purification of tetrameric $^{NAc}$αS through dual SEC steps. (A) BN-PAGE (4-16%) analysis of pooled tetrameric $^{NAc}$αS fraction following first SEC column (SEC-1). (B) Chromatograph of second SEC column (SEC-2) and associated BN-PAGE gel of pooled fractions. Collected fractions were concentrated and the signature alpha-helical spectrum for tetrameric $^{NAc}$αS was obtained from CD secondary structural determination. (C) The 58 kDa band for tetrameric $^{NAc}$αS was then excised and trypsinized for high resolution mass spectrometry, confirming the αS identity with high precision (100% probability); 92% sequence coverage was achieved, including the N-terminal acetyl modification.

Since tetrameric $^{NAc}\alpha$S is a non-covalent complex, SDS electrophoresis denatures the protein to its monomeric form. Under non-denaturing electrophoresis conditions, the tetramer remains intact, displaying a band at ~58 kDa by blue native (BN) PAGE (4-16%) electrophoresis (FIG. 4A). BN-PAGE enables a near-neutral operating pH, which better preserves and separates native protein complexes.[38] Analysis of tetrameric $^{NAc}\alpha$S by SDS-PAGE and BN-PAGE confirmed an $^{NAc}\alpha$S purity of >90% (FIG. 3C and FIG. 4A) following initial SEC purification.

In order to acquire a higher purity of tetrameric $^{NAc}\alpha$S, pooled fractions from the first SEC column were concentrated with a 3 kD centrifugal filter and injected anew onto the Sephacryl column, yielding tetrameric $^{NAc}\alpha$S with >98% purity (FIG. 4B). This second SEC step resulted in an outstanding tetrameric $^{NAc}\alpha$S purity level; however, the isolable protein quantity was diminished by approximately one-third—resulting in a choice between protein yield versus purity. Secondary structural analyses of the tetrameric $^{NAc}\alpha$S sample (FIG. 4B) revealed ~30% alpha-helical content based on a CD structural algorithm, with the second SEC step increasing the alpha-helical content by +10%. The enhanced $\beta$-structure selection (BeStSel) algorithm developed by Micsonai et al.[39] was used as this method provides accurate predictions of protein secondary structures with a Pearson correlation coefficient superior to most presently used algorithms. Its high reliability in helical discrimination allowed us to further elucidate the effectiveness of our purification platform.

Purified tetrameric $^{NAc}\alpha$S was additionally extracted from the BN-PAGE gel and analyzed by mass spectrometry (MS) following trypsinization. The digested sample was analyzed by a Waters Synapt G2Si mass spectrometer system and scrutinized using the ProteinLynx Global Server (PLGS, Waters Corp.) search algorithm against Uniprot's Human database. MS analysis of the corresponding fragments (92% coverage) confirmed the identity of the protein as $\alpha$S with 100% probability and established the successful incorporation of the N-terminal acetyl group (FIG. 4C). Taken together with the signature $\alpha$-helical CD spectrum observed for this sample, BN-PAGE and MS analysis confirm that we have successfully developed a detergent-free protocol for purification of recombinant native tetrameric $^{NAc}\alpha$S.

3.5 Quantification of Yield and Purity Throughout the Purification Cascade

The amount of protein was quantified following each step of the purification process using a Bradford assay, and protein purity was determined based on electrophoresis gel images using ImageJ quantification (Table 1). From a 1 L culture, almost 4 mg of tetrameric $^{NAc}\alpha$S could be isolated following a single SEC step with a purity level of 93%, which is four times the yield reported by Wang and coworkers[20] for their non-native $\alpha$S construct derived from a GST fusion protein. If downstream experiments require a more stringent purity level, an enhancement to >98% could be achieved following a second SEC step, however the overall yield is reduced to 2.6 mg per L culture, which is still more than double the reported yield of Wang and coworkers. The established yields following the first SEC column indicate a tetramer:monomer ratio of approximately 1 to 2.5. Of note, monomeric $^{NAc}\alpha$S purified through this protocol was not as pure as $^{NAc}\alpha$S purified through the traditional "harsh" method that includes boiling and acid treatment, nor was the yield as high. Thus, research focused on the monomeric conformer should be limited to traditional purification methods.[27, 28, 35] Notably, for research focused on the tetrameric conformer, we have demonstrated a reliable and convenient method herein for accessing tetrameric $^{NAc}\alpha$S in a detergent-free regime. Moreover, flash-freezing tetrameric $^{NAc}\alpha$S for extended storage does not compromise the conformational stability of the protein complex based on CD structural analyses.

TABLE 1

Protein Yield and Purity

| Purification of Tetrameric $^{NAc}\alpha$S | Total protein/L culture (mg) | Purity |
|---|---|---|
| Step 1 - $(NH_4)_2SO_4$ Precipitation | 52.8 | — |
| Step 2 - Anion Exchange | 15.6 | — |
| Step 3 - Size Exclusion (Tetramer) | 3.8 | 93% |
| Step 3 - Size Exclusion (Monomer) | 9.8 | 86% |
| Step 4 - $2^{nd}$ SEC (pure Tetramer) | 2.6 | >98% |

3.6 Extension of tetrameric $^{NAc}\alpha$S purification protocol to non-acetylated $\alpha$S ($^{non-AC}\alpha$S)

Since N-terminal acetylation has been demonstrated to increase the helical propensity of $\alpha$S, these studies were replicated with non-acetylated $\alpha$S ($^{non-AC}\alpha$S) in contemplation of the role of this molecular feature. Even in the presence of helical stabilizing detergents, tetrameric $^{non-AC}\alpha$S has not previously been observed[21], so we sought to determine whether or not our mild purification protocol for tetrameric $^{NAc}\alpha$S would enable isolation of a helical tetramer population when applied to $^{non-AC}\alpha$S.

Figures 5A, 5B:
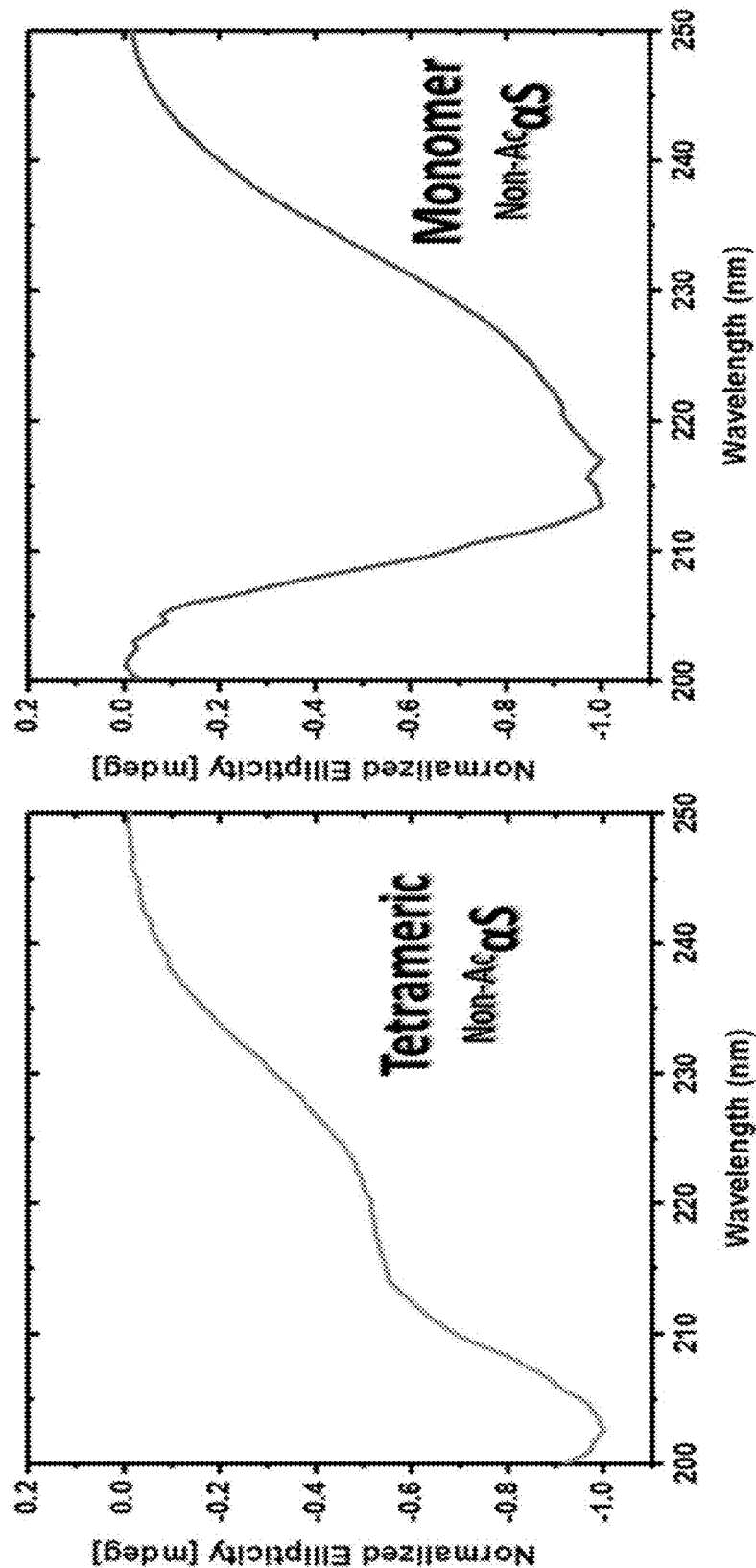
FIG. 5A-B. Secondary structural analysis of $^{non-Ac}$αS following SEC purification. (A) CD spectrum revealing a tetramer/monomer $^{non-Ac}$αS ensemble. (B) CD spectrum of $^{non-Ac}$αS from samples pooled and concentrated from the monomeric region indicating β-sheet formation.

Enrichment of $^{non-AC}\alpha$S proceeded as for $^{NAc}\alpha$S through the anion exchange chromatography step, with no discernible differences based on SDS-PAGE analysis. However, upon application of enriched $^{non-AC}\alpha$S to the Sephacryl size exclusion column, a noticeable shift in the relative peak sizes for the tetrameric and monomeric regions was observed, with the monomeric fraction even more favored relative to the ratio observed for $^{NAc}\alpha_S$ (5:1 monomer: tetramer ratio for $^{non-AC}\alpha$S vs 2.6:1 ratio for $^{NAc}\alpha$S). We proceeded to isolate the fractions in the higher molecular weight tetrameric region and found that not only was the amount of $^{non-AC}\alpha$S protein isolated in this fashion less than its $^{NAc}\alpha$S counterpart (0.57 mg vs 1.9 mg per 400 ml culture), but that the CD spectrum displayed a lower alpha-helical content and more random coiling (FIG. 5A-B). Furthermore, the $^{non-AC}\alpha$S monomeric fraction was noticeably less stable than the analogous monomeric $^{NAc}\alpha$S sample, as it displayed susceptibility to aggregation upon elution and concentration as evidenced by the β-sheet structural features apparent in its CD spectrum instead of the disordered nature expected of monomeric $\alpha$S. Collectively, this is further evidence of a role for N-terminal acetylation in enhancing the structural stability of the helical tetrameric conformation and in delaying aggregation onset from the monomeric form, consistent with previous reports.[16, 18, 21]

4. Conclusions

This work represents a robust and straightforward methodology for obtaining tetrameric $^{NAc}\alpha$S through a recombinant co-expression platform, generating the physiologically relevant human variant that carries an N-terminal acetyl group. This tetrameric conformer has steadily gained attention in the scientific community since its controversial discovery, yet access has been limited to purification protocols utilizing chemical cross-linkers, detergents, or non-native sequences that may compromise the physiological relevance. We have obtained tetrameric $^{NAc}\alpha$S with >98% purity and confirmed its apparent molecular weight (58 kDa) as well as its signature alpha-helical secondary structure. As has been reported for in vivo experiments, tetrameric $^{NAc}\alpha$S exists in lower quantities in comparison to its monomeric conformational counterpart. Despite the apparent stability of tetrameric $^{NAc}\alpha$S implied by its aggregation resistance, this protein complex is metastable and dissociates under dilute conditions. Hence, we favored high total protein concentrations throughout our purification cascade and employed a combination of mild purification steps, including ammonium sulfate precipitation and low pressure chromatographic protocols. For anion exchange purification, we chose a small particle size resin (34 Å) which was expected to preclude large distortions among the noncovalent protein complex. Size exclusion separation was carried out at low flow rates (<0.5 mL/min) and low pressures (<0.15 MPa) in order to recover high purity tetrameric $^{NAc}\alpha$S in good yield (~2 mg per L of E. coli culture) without compromising its helical structure. Our approach brings the elusive but important tetrameric $^{NAc}\alpha$S conformer within reach and will enable the systematic biochemical and biophysical studies that have been hampered heretofore by limited access to this potential PD therapeutic target.

REFERENCES

[1] D. E. Mor, S. E. Ugras, M. J. Daniels, H. Ischiropoulos, Dynamic structural flexibility of α-synuclein. Neurobiol. Dis. 88 (2016) 66-74.

[2] U. Dettmer, D. Selkoe, T. Bartels, New insights into cellular α-synuclein homeostasis in health and disease. Curr. Opin. Neurobiol. 36 (2016) 15-22.

[3] T. C. Pochapsky, From intrinsically disordered protein to context-dependent folding: The α-synuclein tetramer is teased out of hiding. Proc. Natl. Acad. Sci. U.S.A. 112 (2015) 9502-9503.

[4] Y. Cote, P. Delarue, H. A. Scheraga, P. Senet, G. G. Maisuradze, From a Highly Disordered to a Metastable State: Uncovering Insights of α-Synuclein. ACS Chem. Neurosci. (2018).

[5] H. A. Lashuel, C. R. Overk, A. Oueslati, E. Masliah, The many faces of α-synuclein: from structure and toxicity to therapeutic target. Nat. Rev. Neurosci. 14 (2013) 38-48.

[6] T. R. Alderson, J. L. Markley, Biophysical characterization of α-synuclein and its controversial structure. Intrinsically Disord. Proteins 1 (2013) 18-39.

[7] D. L. Abeyawardhane, R. D. Fernandez, C. J. Murgas, D. R. Heitger, A. K. Forney, M. K. Crozier, H. R. Lucas, Iron Redox Chemistry Promotes Antiparallel Oligomerization of alpha-Synuclein. J. Am. Chem. Soc. (Submitted 2017).

[8] G. M. Moriarty, M. K. Janowska, L. Kang, J. Baum, Exploring the accessible conformations of N-terminal acetylated α-synuclein. FEBS Lett. 587 (2013) 1128-1138.

[9] J. C. Bridi, F. Hirth, Mechanisms of α-Synuclein Induced Synaptopathy in Parkinson's Disease. Front. Neurosci. 12 (2018) 80.

[10] T. Bartels, J. G. Choi, D. J. Selkoe, α-Synuclein occurs physiologically as a helically folded tetramer that resists aggregation. Nature 477 (2011) 107-110.

[11] U. Dettmer, A. J. Newman, F. Soldner, E. S. Luth, N. C. Kim, V. E. von Saucken, J. B. Sanderson, R. Jaenisch, T. Bartels, D. Selkoe, Parkinson-causing α-synuclein missense mutations shift native tetramers to monomers as a mechanism for disease initiation. Nat. Commun. 6 (2015) 7314.

[12] U. Dettmer, A. J. Newman, E. S. Luth, T. Bartels, D. Selkoe, In vivo cross-linking reveals principally oligomeric forms of α-synuclein and β-synuclein in neurons and non-neural cells. J. Biol. Chem. 288 (2013) 6371-6385.

[13] J. P. Anderson, D. E. Walker, J. M. Goldstein, R. de Laat, K. Banducci, R. J. Caccavello, R. Barbour, J. Huang, K. Kling, M. Lee, L. Diep, P. S. Keim, X. Shen, T. Chataway, M. G. Schlossmacher, P. Seubert, D. Schenk, S. Sinha, W. P. Gai, T. J. Chilcote, Phosphorylation of Ser-129 is the dominant pathological modification of alpha-synuclein in familial and sporadic Lewy body disease. J. Biol. Chem. 281 (2006) 29739-29752.

[14] A. Ohrfelt, H. Zetterberg, K. Andersson, R. Persson, D. Secic, G. Brinkmalm, A. Wallin, E. Mulugeta, P. T. Francis, E. Vanmechelen, D. Aarsland, C. Ballard, K. Blennow, A. Westman-Brinkmalm, Identification of novel α-synuclein isoforms in human brain tissue by using an online nanoLC-ESI-FTICR-MS method. Neurochem. Res. 36 (2011) 2029-2042.

[15] A. Iyer, S. J. Roeters, N. Schilderink, B. Hommersom, R. M. Heeren, S. Woutersen, M. M. Claessens, V. Subramaniam, The Impact of N-terminal Acetylation of α-Synuclein on Phospholipid Membrane Binding and Fibril Structure. J. Biol. Chem. 291 (2016) 21110-21122.

[16] T. Bartels, N. C. Kim, E. S. Luth, D. J. Selkoe, N-alpha-acetylation of α-synuclein increases its helical folding propensity, GM1 binding specificity and resistance to aggregation. PLoS One 9 (2014) e103727.

[17] I. Dikiy, D. Eliezer, N-terminal acetylation stabilizes N-terminal helicity in lipid- and micelle-bound α-synuclein and increases its affinity for physiological membranes. J. Biol. Chem. 289 (2014) 3652-3665.

[18] L. Kang, G. M. Moriarty, L. A. Woods, A. E. Ashcroft, S. E. Radford, J. Baum, N-terminal acetylation of α-synuclein induces increased transient helical propensity and decreased aggregation rates in the intrinsically disordered monomer. Protein Sci. 21 (2012) 911-917.

[19] A. S. Maltsev, J. Ying, A. Bax, Impact of N-terminal acetylation of α-synuclein on its random coil and lipid binding properties. Biochemistry 51 (2012) 5004-5013.

[20] W. Wang, I. Perovic, J. Chittuluru, A. Kaganovich, L. T. Nguyen, J. Liao, J. R. Auclair, D. Johnson, A. Landeru, A. K. Simorellis, S. Ju, M. R. Cookson, F. J. Asturias, J. N. Agar, B. N. Webb, C. Kang, D. Ringe, G. A. Petsko, T. C. Pochapsky, Q. Q. Hoang, A soluble α-synuclein construct forms a dynamic tetramer. Proc. Natl. Acad. Sci. U.S.A. 108 (2011) 17797-17802.

[21] A. J. Trexler, E. Rhoades, N-Terminal acetylation is critical for forming α-helical oligomer of α-synuclein. Protein Sci. 21 (2012) 601-605.

[22] D. Eliezer, E. Kutluay, R. Bussell, G. Browne, Conformational properties of α-synuclein in its free and lipid-associated states 11 Edited by P. E. Wright. J. Mol. Biol. 307 (2001) 1061-1073.

[23] A. C. Ferreon, Y. Gambin, E. A. Lemke, A. A. Deniz, Interplay of alpha-synuclein binding and conformational switching probed by single-molecule fluorescence. Proc. Natl. Acad. Sci. U.S.A. 106 (2009) 5645-5650.

[24] M. Zhu, J. Li, A. L. Fink, The association of alpha-synuclein with membranes affects bilayer structure, stability, and fibril formation. J. Biol. Chem. 278 (2003) 40186-40197.

[25] M. Johnson, A. T. Coulton, M. A. Geeves, D. P. Mulvihill, Targeted amino-terminal acetylation of recombinant proteins in E. coli. PLoS One 5 (2010) e15801.

[26] J. Baum, Accessible Conformations of N-Terminal Acetylated Alpha-Synuclein: Implications for Fibril Formation. Biophys. J. 106 5a.

[27] H. R. Lucas, S. Debeer, M. S. Hong, J. C. Lee, Evidence for copper-dioxygen reactivity during alpha-synuclein fibril formation. J. Am. Chem. Soc. 132 (2010) 6636-6637.

[28] H. R. Lucas, J. C. Lee, Copper(II) enhances membrane-bound α-synuclein helix formation. Metallomics 3 (2011) 280-283.

[29] A. Binolfi, A. A. Valiente-Gabioud, R. Duran, M. Zweckstetter, C. Griesinger, C. O. Fernandez, Exploring the structural details of Cu(I) binding to α-synuclein by NMR spectroscopy. J. Am. Chem. Soc. 133 (2011) 194-196.

[30] D. L. Abeyawardhane, D. R. Heitger, R. D. Fernandez, M. K. Crozier, J. Wolver, H. R. Lucas, Copper-Induced Radical Coupling of alpha-Synuclein. ACS Chem. Neurosci. (Submitted 2018).

[31] M. C. Miotto, A. A. Valiente-Gabioud, G. Rossetti, M. Zweckstetter, P. Carloni, P. Selenko, C. Griesinger, A. Binolfi, C. O. Fernández, Copper binding to the N-terminally acetylated, naturally occurring form of alpha-synuclein induces local helical folding. J. Am. Chem. Soc. 137 (2015) 6444-6447.

[32] M. S. Jackson, J. C. Lee, Identification of the minimal copper(II)-binding alpha-synuclein sequence. Inorg. Chem. 48 (2009) 9303-9307.

[33] B. Fauvet, M. B. Fares, F. Samuel, I. Dikiy, A. Tandon, D. Eliezer, H. A. Lashuel, Characterization of semisynthetic and naturally Nα-acetylated α-synuclein in vitro and in intact cells: implications for aggregation and cellular properties of α-synuclein. J. Biol. Chem. 287 (2012) 28243-28262.

[34] U. Dettmer, A. J. Newman, V. E. von Saucken, T. Bartels, D. Selkoe, KTKEGV repeat motifs are key mediators of normal α-synuclein tetramerization: Their mutation causes excess monomers and neurotoxicity. Proc. Natl. Acad. Sci. U.S.A. 112 (2015) 9596-9601.

[35] B. I. Giasson, K. Uryu, J. Q. Trojanowski, V. M. Lee, Mutant and wild type human alpha-synucleins assemble into elongated filaments with distinct morphologies in vitro. J. Biol. Chem. 274 (1999) 7619-7622.

[36] J. C. Lee, H. B. Gray, J. R. Winkler, Copper(II) binding to alpha-synuclein, the Parkinson's protein. J. Am. Chem. Soc. 130 (2008) 6898-6899.

[37] B. Fauvet, M. K. Mbefo, M. B. Fares, C. Desobry, S. Michael, M. T. Ardah, E. Tsika, P. Coune, M. Prudent, N. Lion, D. Eliezer, D. J. Moore, B. Schneider, P. Aebischer, O. M. El-Agnaf, E. Masliah, H. A. Lashuel, α-Synuclein in central nervous system and from erythrocytes, mammalian cells, and *Escherichia coli* exists predominantly as disordered monomer. J. Biol. Chem. 287 (2012) 15345-15364.

[38] G. J. Fiala, W. W. Schamel, B. Blumenthal, Blue native polyacrylamide gel electrophoresis (BN-PAGE) for analysis of multiprotein complexes from cellular lysates. J. Vis. Exp. (2011).

[39] A. Micsonai, F. Wien, L. Kernya, Y. H. Lee, Y. Goto, M. Réfrégiers, J. Kardos, Accurate secondary structure prediction and fold recognition for circular dichroism spectroscopy. Proc. Natl. Acad. Sci. U.S.A. 112 (2015) E3095-3103.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for preparing tetrameric N-terminally acetylated α-synuclein, comprising the steps of:
    transforming an expression system with an expression vector encoding α-synuclein, wherein the expression system does not encode α-synuclein as part of a fusion protein, wherein the expression system expresses a native NatB acetylase complex or ortholog thereof and/or wherein an exogenous NatB acetylase complex or ortholog thereof is co-expressed in the expression system,
    inducing protein expression in the transformed expression system,
    lysing cells in the transformed expression system to produce a cell lysate,
    performing salt precipitation of the cell lysate,
    recovering tetrameric N-terminally acetylated α-synuclein by centrifugation, and
    purifying the tetrameric N-terminally acetylated α-synuclein.

2. The method of claim 1, wherein the expression system is *Escherichia coli*.

3. The method of claim 1, wherein an exogenous NatB acetylase complex or ortholog thereof is co-expressed in the expression system and wherein the exogenous NatB acetylase complex is encoded by the expression vector encoding α-synuclein or a different expression vector.

4. The method of claim 3, wherein the acetylase complex is a *Schizosaccharomyces pombe* acetylase complex.

5. The method of claim 1, wherein the salt precipitation is an ammonium sulfate precipitation and wherein the cell lysate is brought to 25% saturation in a first phase of the ammonium sulfate precipitation and is brought to 50% saturation in a second phase of the ammonium sulfate precipitation.

6. The method of claim 1, wherein the salt precipitation is an ammonium sulfate precipitation and wherein tetrameric N-terminally acetylated α-synuclein is recovered between 30-50% ammonium sulfate saturation.

7. The method of claim 1, wherein the method is performed in the absence of detergent.

8. The method of claim 1, wherein the method is performed in the absence of boiling or acid treatment.

9. The method of claim 1, wherein the step of purifying is performed by anion exchange chromatography followed by size exclusion chromatography.

10. The method of claim 9, wherein pooled fractions recovered from size exclusion chromatography are used as input for a second size exclusion chromatography step.

11. The method of claim 1, wherein the α-synuclein encoded by the expression vector has a sequence as provided in SEQ ID NO: 1.

12. The method of claim 1, wherein each monomer of the recovered tetrameric N-terminally acetylated α-synuclein consists of a sequence having at least 95% identity with SEQ ID NO: 1.

* * * * *

SEQUENCE LISTING

```
<160> NUMBER OF SEQ ID NOS: 3

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 180
<212> TYPE: PRT
<213> ORGANISM: Schizosaccharomyces pombe

<400> SEQUENCE: 2

Met Thr Asp Thr Arg Lys Phe Lys Ala Thr Asp Leu Phe Ser Phe Asn
1               5                   10                  15

Asn Ile Asn Leu Asp Pro Leu Thr Glu Thr Phe Asn Ile Ser Phe Tyr
            20                  25                  30

Leu Ser Tyr Leu Asn Lys Trp Pro Ser Leu Cys Val Val Gln Glu Ser
        35                  40                  45

Asp Leu Ser Asp Pro Thr Leu Met Gly Tyr Ile Met Gly Lys Ser Glu
    50                  55                  60

Gly Thr Gly Lys Glu Trp His Thr His Val Thr Ala Ile Thr Val Ala
65                  70                  75                  80

Pro Asn Ser Arg Arg Leu Gly Leu Ala Arg Thr Met Met Asp Tyr Leu
                85                  90                  95

Glu Thr Val Gly Asn Ser Glu Asn Ala Phe Phe Val Asp Leu Phe Val
            100                 105                 110

Arg Ala Ser Asn Ala Leu Ala Ile Asp Phe Tyr Lys Gly Leu Gly Tyr
        115                 120                 125

Ser Val Tyr Arg Arg Val Ile Gly Tyr Tyr Ser Asn Pro His Gly Lys
    130                 135                 140

Asp Glu Asp Ser Phe Asp Met Arg Lys Pro Leu Ser Arg Asp Val Asn
145                 150                 155                 160

Arg Glu Ser Ile Arg Glu Asn Gly Glu Asn Phe Lys Cys Ser Pro Ala
```

```
                        165                 170                 175
Asp Val Ser Phe
            180

<210> SEQ ID NO 3
<211> LENGTH: 811
<212> TYPE: PRT
<213> ORGANISM: Schizosaccharomyces pombe

<400> SEQUENCE: 3

Met Arg Arg Ser Gly Ser Lys Glu Ser Thr Ile Val Tyr Ser Ala Leu
1               5                   10                  15

Ser Leu Ala Gln Ala Gly Arg Gly Pro Glu Ala Leu Ala Leu Leu Glu
            20                  25                  30

Pro Leu Lys Ser Thr Pro Ile Asn Ser Leu Glu Leu Leu Asp Ile Ile
        35                  40                  45

Gln Ala Val Tyr Asp Asp Gln Lys Lys Gly Glu Glu Ser Phe Val Phe
    50                  55                  60

Trp Glu Lys Phe Leu Gln Thr Tyr Gly Lys Gln Lys Asn Leu Leu
65              70                  75                  80

Ala Tyr Phe Lys Ala Ser Ile Arg Ile Lys Ser Leu Ser His Gln Arg
                85                  90                  95

Lys Ala Ala Val Glu Leu Gln Lys Asn Phe Pro Ser Arg Lys His Thr
            100                 105                 110

Leu Trp Val Ile Ser Ser Leu Tyr Leu Leu Ser Lys Lys Ser Glu Asn
        115                 120                 125

Glu Val Glu Gln Arg Leu Leu Lys Ala Leu Ala Glu Lys Thr Ala Lys
130                 135                 140

Leu Ile Phe Glu Lys Pro Thr Gly Tyr Ile Asp Ser Cys Glu Glu Phe
145                 150                 155                 160

His Leu Tyr Leu Asp Val Leu Leu Val Gly Asp Lys Asp Arg Ala
                165                 170                 175

Leu Asp Ala Leu Ile His Gln Asp Ala Asp Arg Phe Val Asp Ala Asp
            180                 185                 190

Ala Asp Leu Leu Arg Lys Leu Glu Leu Leu Ala Ser Cys Ala Arg
            195                 200                 205

Trp Asp Ser Leu Phe Thr Phe Ser Leu Ser Leu Phe Gln Thr Gly Asn
210                 215                 220

Thr Asp Trp Lys Val Cys Lys Ala Leu Leu Asp Ser Ala Ser Asn Asp
225                 230                 235                 240

Asp Ser Lys Leu Val Pro Leu Lys Asp Cys Ile Leu Lys Ala Leu Ser
                245                 250                 255

Thr Ser Ser Thr Lys Arg Asn Leu His Leu Leu Trp Ile Glu Ala Ser
            260                 265                 270

Ala Arg Phe Phe Pro Glu Glu His Glu Ser Ala Leu Leu Gly Tyr Ile
        275                 280                 285

Lys Lys Leu Tyr Met Lys Pro Ile Val Phe Glu Asp Leu Arg Pro Tyr
    290                 295                 300

Leu Leu Lys Leu Asn Val Asp Ala Gln His Arg Leu Leu Asp Ala Phe
305                 310                 315                 320

Lys Leu Ala Asp Leu Gly Glu Ser Asn Glu Ser Gln Lys Val Asp Lys
                325                 330                 335

Leu Tyr Ala Glu Val Leu Leu Leu Lys Ile His Phe Leu Leu Phe Glu
            340                 345                 350
```

```
Ser Phe Thr Ala Glu Ser Val Val Asp Tyr Val Arg Arg Cys Phe Val
            355                 360                 365

Ala Phe Glu Lys Gly Leu Ser Leu Ser Lys Gly Leu Leu Pro Thr Asp
370                 375                 380

Phe Thr His Gly Tyr Glu Ala Leu Leu Leu Ala Val His Ser Leu Ile
385                 390                 395                 400

Tyr Met Trp Glu Gly Asn Lys Asp Leu Lys Pro Ala Glu Lys Gln Ala
                405                 410                 415

Leu Ile Phe Asp Ala Ile Cys Leu Leu Glu Lys Gly Ile Thr Tyr Ser
            420                 425                 430

Gln His Asn Phe His Leu Lys Leu Pro Leu Ile Arg Leu Tyr Leu Leu
            435                 440                 445

Leu Asp Gly Gly Phe Pro Ala Ala Ala Lys Val Tyr Asp Thr Met Ser
450                 455                 460

Ile Lys Gln Ile Gln Asn Asp Thr Leu Asp His Tyr Leu Leu Thr Arg
465                 470                 475                 480

Ala Thr Thr Tyr Tyr Pro Ser Ser Val Thr Ser His Tyr Ile Asn Ser
                485                 490                 495

Ser Leu Lys Ile Tyr Gly Ser Asn Glu Phe Glu Thr Pro Glu Met Ile
            500                 505                 510

Ser Met Ala Tyr Glu Asp Gly Ala Tyr Ser Gln Ile Glu Asp Met Arg
            515                 520                 525

Asn Phe Arg Ser Arg Leu Asp His Ser Thr Trp Lys Ser Ile Ser Leu
            530                 535                 540

Val Glu Arg Ala Arg Ile His Tyr Leu Thr Ala Phe Lys Pro Pro Lys
545                 550                 555                 560

Gln Tyr Leu Pro Lys Cys Ser Pro Lys Asp Asn Arg Asp Leu Lys
                565                 570                 575

Val Phe Ala Asp Tyr Gly Ser Asp Lys Leu Pro Thr Val Glu Glu Ser
            580                 585                 590

Leu Arg Asn Ser Pro Lys Pro Asp Thr Leu Trp Ile His Leu Thr Val
            595                 600                 605

Ile Gly His Ser Leu Val Gln Asp Ser Ile Val Asn Gly Asp Phe Glu
610                 615                 620

Lys Ala Val Leu Ser Ala Lys Glu Met Glu Val Leu Cys Glu Asn Asn
625                 630                 635                 640

Asp Leu Ser Lys Gln Leu Thr Ser Glu Ile Val His Met Lys Leu
                645                 650                 655

Leu Ile Gln Leu Gly Leu Leu Ser Val Lys Val Lys Asn Gly Asp Tyr
            660                 665                 670

Glu Asn Ser Ser Phe Glu Thr Ile Glu Asn Leu Ile Glu Ser Phe Asp
            675                 680                 685

Tyr Glu Asn Ser Thr Pro Leu Ser Gln Leu Thr Lys Tyr Thr Glu Ile
690                 695                 700

Ile Asn Asp Leu Ile Thr Cys Leu Asn Ser Phe Leu Tyr His Val Ser
705                 710                 715                 720

Ala Thr Lys Lys Lys Glu Phe Thr Arg Gln Tyr Gln Leu Leu Lys Asn
                725                 730                 735

Ile Ser Ser Asn Lys Leu Gly Ser Ile Ser Gly Ile Thr Lys His Lys
            740                 745                 750

Lys Lys Ala Ala Arg Lys Tyr Val Ser Glu Leu Leu Ser Asn Ser Trp
755                 760                 765

Leu Ser Asn Leu Ser Glu Thr Gln Val Pro Tyr Asp Pro Lys Phe Ala
```

```
                    770               775               780
Lys Gln Val Gly Glu Gly Met Ile Asp Ser Tyr Ile Gln Thr Thr Asp
785                     790               795                 800

Ala Val Ser Lys Leu Pro Lys Phe Val Lys Phe
                805             810
```